United States Patent [19]

Murray

[11] Patent Number: 4,659,572

[45] Date of Patent: Apr. 21, 1987

[54] BURN WOUND DRESSING MATERIAL

[75] Inventor: Douglas G. Murray, Willowdale, Canada

[73] Assignee: Her Majesty the Queen in right of Canada, as represented by the Minister of National Defence, Canada

[21] Appl. No.: 796,759

[22] Filed: Nov. 12, 1985

Related U.S. Application Data

[63] Continuation-in-part of Ser. No. 722,435, Apr. 15, 1985, abandoned, and Ser. No. 406,523, Aug. 9, 1982, abandoned, said Ser. No. 722,435, is a continuation of Ser. No. 456,446, Jan. 7, 1983, abandoned.

[51] Int. Cl.$^4$ .............................................. A61K 31/74
[52] U.S. Cl. ..................................... 424/448; 514/774
[58] Field of Search ............................ 424/27, 28, 78; 624/896, 897; 524/22, 23; 514/774

[56] References Cited

U.S. PATENT DOCUMENTS 4,265,233  5/1981  Sugitachi et al. ................... 128/156

Primary Examiner—Leonard Schenkman
Attorney, Agent, or Firm—Nixon & Vanderhye

[57] ABSTRACT

A burn wound-adherent dressing material comprising a complex of gelatin and a water-soluble resin material such as polyethylenimine. The dressing material may be in the form of a preformed film or in the form of an aqueous coating which sets to a gel and dries to a continuous wound-adherent film in situ.

19 Claims, No Drawings

BURN WOUND DRESSING MATERIAL

CROSS-REFERENCE TO REALTED APPLICATIONS

This application is a continuation-in-part of my earlier application Ser. No. 722,435 filed Apr. 15, 1985 which, in turn, was a continuation of earlier application Ser. No. 456,446 filed Jan. 7, 1983, both now abandoned. This application is also a continuation-in-part of my earlier application Ser. No. 406,523 filed Aug. 9, 1982, now abandoned.

BACKGROUND OF THE INVENTION

This invention relates to surgical dressings and in particular to the covering of a wound, lesion or the like with an adherent film to effect protection therefor during the healing process.

A very large number of people are seriously burned in domestic and industrial accidents every year, and the number of these victims which die in spite of intensive medical care is distressingly high. In Canada, the number of burn injuries requiring hospital admission approaches 25,000 per year. In the United States, about 130,000 are hospitalized annually because of burns; of these, 70,000 require intensive care at a cost exceeding $300,000,000, and 10,000 die.

The problem of burn treatment is even more acute in areas of the world in which there is armed conflict, since many of the weapons of modern warfare either directly or indirectly cause burns to both military personnel and civilians. In time of war the demands on medical facilities and supplies are very severe, and the mortality rate among burn victims is greatly increased.

In a third degree burn, the full thickness of the skin has been destroyed. The complete absence of "skin" cells in the burned area means that a new covering of skin will not spontaneously form there except by the very slow proliferation of healthy cells at the edges of the burn. One treatment is to remove a thin sheet of healthy skin from the patient's own body and graft it on to the burned area. Only a partial thickness of skin is removed, so that the cells in the remaining layer of skin can regenerate a full thickness in the area from which the graft was harvested. In cases of burns covering 50% or more of the body surface area, this grafting procedure will be a lengthy process carried out in several stages because of the time required for regeneration of skin on the harvested sites.

In the intervening period between hospitalization and grafting, two very serious problems are caused by the absence of skin in the area of the burn. One of the most important functions of normal skin is to restrict the loss of body water by evaporation. The dramatic increase in water loss caused by destruction of the skin produces a large rate of heat loss due to the cooling effect of evaporation. In order to maintain a normal body temperature, the metabolic rate must increase, and a rapid depletion of fat and protein reserves ensues. The other serious problem caused by the absence of skin is bacterial invasion. If this invasive infection is not restricted, the high bacteria population makes the wound unsuitable for skin grafting. The victim of a major burn who receives no treatment for this infection will ultimately die from it.

After removal of the layer of dead tissue (eschar) lying on top of the burned area, it is desirable to cover the wound with a dressing which will control water loss and assist the body's own defences in controlling bacterial proliferation until skin grafting can be carried out.

Two natural materials, pigskin and human skin from cadavers, are regarded as very effective burn dressings. These materials can, under favourable circumstances, adhere to the wound very well and effectively control water loss and infection. The problem is that the body recognizes these biological materials as foreign substances, and begins a cellular response to reject them. Because of this, these biological dressings must be replaced every 2 to 4 days. The other major drawback of these materials is their high cost. Cadaver skin at $80 and up per square foot, and pig skin at about $30 per square foot, are so expensive that physicians can be reluctant to use them except in cases in which they are essential for survival of the patient.

The disadvantages associated with these biological materials have given rise to the preparation of a large number of synthetic substitutes. The more effective of these have consisted of a foam, velour, or fibrous mat laminated to a synthetic resin film. Adhesion to the wound occurs by growth of tissue into the interstices of the foam or fibres, and the film controls loss of body water and prevents entry of bacteria. This basic approach has some inherent drawbacks. Since the adhesion depends on ingrowth, some time must elapse before the dressing is firmly adherent to the wound. A more serious problem in many cases has been the tenacious adherence that eventually does take place. Removal of the dressing can then be a traumatic procedure which may produce excessive bleeding and leave fragments of the synthetic material in the wound. These fragments may delay the healing of the wound when skin grafting is carried out.

Two laminates of this type are on the market. One of these, a laminate of microporous polypropylene and reticulated polyurethane foam is sold under the trademark EPIGARD by Parke, Davis and Co. For a variety of reasons, EPIGARD has not been widely accepted for clinical use by surgeons who treat burn patients. The other laminate is sold under the trademark BIOBRANE by Hall-Woodroof Inc. It is a composite of a flexible nylon fabric and an ultra-thin silicone rubber membrane. The high cost of BIOBRANE is a very serious drawback which may limit its acceptance.

A radically different type of burn dressing has been developed by I. V. Yannas and J. F. Burke and coworkers in the United States. Their approach has been to produce a material which slowly biodegrades at the wound surface and is assimilated by the body. During this biodegradation, the dressing not only restricts water loss and controls infection, but also acts as a tissue culture medium. Ultimately, migration of epidermal cells forms a new skin over the wound site. At the present state of development of their film, the healing of only relatively small wounds by this elegant process is possible. The film can be used to advantage on large wounds, but skin grafting is still required at a later stage. A commercial form of the film, when available, will probably be quite expensive.

In U.S. Pat. No. 3,165,560 which issued Jan. 5, 1965, John F. Suter teaches the use of a gelatin/polyalkylene oxide composition in the form of continuous films of improved extensibility and flexibility as compared to gelatin films and which have improved tensile strength and toughness as compared to polyalkylene oxide films. The films are used, for example, in packaging and photographic supplies. There is no teaching or suggestion of use as wound dressings.

U.S. Pat. No. 4,265,233 of May 5, 1981 in the name of Sugitachi et al teaches a material for the healing of wounds having blood coagulation Factor XIII fixed thereto. A wide variety of polymers including gelatin and other polymers, such as poly(ethylene oxide) and polyethylenimine, are specified as useful materials. It is emphasized that this type of dressing operates on the basis of the formation of stabilized fibrin at the wound site. The materials are preferably body absorbable. Moreover, any materials of which blood coagulation Factor XIII is a significant component would be expected to be very expensive. It is also emphasized that this teaching in no way teaches or suggests the use of combinations of gelatin and other polymers.

It is therefore an object of my invention to fill the need for an effective yet inexpensive wound dressing.

It is a further object of my invention to provide a burn wound-adherent dressing material which forms a naturally wound-adherent covering over the burn wound which controls water-loss and minimizes ingress of exogenous micro-organisms during the healing process or until it is removed to permit skin grafting.

SUMMARY OF THE INVENTION

According to the invention, a burn wound-adherent dressing material is provided, comprising a complex of gelatin and a water-soluble resin material.

The dressing material according to the invention may be in the form of a preformed film or in the form of an aqueous coating which sets to a gel and dries to a continuous burn wound-adherent film in situ.

It is important to the invention that the polymers used in the production of the film are water-soluble and the resulting film adheres to the wound without the need of additional securing devices. Also important is the ease of release of the film from the wound. Preferably, the films should be sufficiently transparent to permit observation of the wound and the possible appearance of purulence beneath the film.

It is emphasized that applicant's novel burn wound dressing material comprises a combination of gelatin and a water-soluble resin material, such as polyethylenimine, which is not merely a simple mixture but a complex which is formed by interaction of the polymer chains of the two materials.

In particular, complexes of gelatin and poly(ethylene oxide) (PEO); and gelatin and polyethylenimine (PEI) have been found to be specially effective.

Preformed Films

Tests of these materials were carried out using juvenile domestic pigs, and the following model wounds were created to simulate those encountered in clinical practice:

(i) Donor site. From areas on the back measuring 4×3 cm, about 0.3-0.4 mm of skin were removed with a Silver dermatome. This top layer of skin is typical of the material used for skin grafting, and the area from which it is removed is known as a donor site. Donor sites in human patients should be protected from water loss and infection until they heal.

(ii) Exposed fascia. Small areas of healthy skin and the layer of fat beneath were surgically removed, thus exposing the thin, dense tissue covering the muscle. This thin covering is called fascia.

(iii) Full thickness burn. Burns were administered under anaesthetic using a custom made, electrically heated template measuring 5×5 cm. The burns destroyed the full thickness of the skin. The site of the burn was treated in one of two ways:

(a) after 5-7 days the dead tissue (eschar) in the burned area was removed surgically, thus exposing a surface of subcutaneous fat.

(b) after 14 days, the eschar was removed, exposing granulation tissue which had formed beneath it.

Those familiar with scientific studies of the problem of temporary closure of large, open wounds caused by the loss of skin known that the single most important property of a prosthetic skin material is adherence to the wound base. The gelatin-PEO and gelatin-PEI films of the present invention showed very rapid initial adherence to the moist debrided surface of each of the model wounds described above. Firm adhesion seldom required more than 1-2 minutes, and in some cases excellent adhesion was obtained on contact. In contrast to many other dressing materials, there was no need to secure the films on the wounds with sutures, staples, tape, etc., until significant adhesion took place.

The rapid initial adhesion of gelatin-PEO and gelatin-PEI films requires that the surface of the wound be moist. The natural moisture supplied by the wound is often quite satisfactory. If the wound is too dry, it can be moistened with water, physiological saline, or other suitable fluid; if the wound is too wet, rapidly adhesion may not occur, but the excess fluid can be removed by use of absorbent fabric such as surgical gauze. In practice, preparation of the wound and adjustment of the moisture level to one suitable for rapid adhesion of the films is an easily acquired art.

The length of time that the gelatin-PEO and gelatin-PEI films remained adherent to model wounds depended on several factors. In the case of burn model (iiia), over a period of several days there was generally a gradual loss of adhesion at the edges. This loss of edge adhesion is due in part to the upward force exerted by a growing layer of crusty exudate which forms in the small area between the edge of film and the edge of the wound. Good adhesion in the central part of the wound persisted in some cases for as long as 14 days. Even after periods as long as this, the areas to which the films had maintained good adhesion appeared healthy and free of frank infection, even though no bacteriacial agent of any kind was applied to the wound at any time.

Adhesion to donor sites for periods of 6 to 10 days has been observed. Periods of this duration, depending on the thickness of the layer of skin originally removed, the wound is healed almost completely, without any obvious complications.

Thus, an advantage of films of the present invention over dressings which depend on ingrowth for adhesion is their ease of removal. By merely soaking the films adhering to the wounds in tap water or physiological saline for 15 minutes at the temperature of the wound surface, the adhesion is greatly diminished and the films become soft. They can then be removed by gentle scraping or in some cases by simply peeling them off.

Another distinct asset of the gelatin-PEI material and in most cases of the gelatin-PEO material is they they are sufficiently transparent when adhering to the wound to permit visual detection of areas of serious infection without removal of the film.

Turning now to polyethylenimine as the water-soluble polymer, films composed of gelatin of Bloom #150 and a grade of PEI called "Polymin P ®" from BASF, having a molecular weight of about 50,000, and having weight ratios of gelatin to PEI of 7:3, 1:1, 45:55, 40:60, and 35:65, were prepared and found to have similar properties in the dry state. Both the 1:1 and 35:65 materials were tested on model debrided burn wounds and found to give satisfactory adhesion. The preferred ratio is 1:1, but ratios falling in the range 9:1 to 3:7 should be suitable.

The invention is not restricted to one grade of gelatin or to a specific grade of PEI. Gelatins of Bloom #80 to 350 and PEI's of a molecular weight range of 10,000 to 100,000 are contemplated.

The preferred embodiment of the gelatin-PEI film is prepared by dissolving 1 part of gelatin of Bloom #150 and 2 parts of a 50% aqueous solution of PEI called "Polymin P ®" in 21-29 parts distilled water, pouring the solution onto a flat surface, and allowing the film to dry in air at room temperature. This gives a film of thickness 0.15-0.25 mm, depending on the amount of water used. The thickness of the preferred gelatin-PEI film used on model wounds has ranged from 0.15 to 0.35 mm. The preferred thickness is 0.20 mm for donor sites, and 0.15 mm for wounds of types (ii), (iiia) and (iiib). In general, the range of useful thicknesses for gelatin-PEI films should be about 0.05 to 0.35 mm.

EXAMPLE 1

1 part gelatin of Bloom 150 from the Davis Gelatine Co. was dissolved in 20 parts distilled water at about 50° C. and this solution was mixed with a solution of 2 parts of a commercial 50% aqueous solution of PEI (Polymin P ® made by BASF) in 9 parts of distilled water. The resulting solution was cooled to 25° to 30° C. and poured onto a flat, smooth sheet of polystyrene and left to dry in air at room temperature. When dry, the thickness of the film was about 0.15 mm.

In biocompatibility tests, subcutaneous implantation of gelatin-PEO and gelatin/PEI specimens in a rabbit caused no haemorrhage, hyperaemia, formation of exudate, or formation of capsule after 72 hours. In further tests on gelatin/PEO specimens no signs of toxicity were detected over a 3 day period after intravenous injection into mice of an extract of the film in physiological saline and no signs of toxicity were observed over a period of 3 days when a solution of the film in physiological saline was injected intraperitoneally in mice. The rate and nature of the healing in the presence of a gelatin/PEO film was essentially similar to that of a control wound.

It is expected that these materials would be used as (i) temporary dressings on third degree burn wounds after removal of the dead tissue and up to the time at which skin grafting could be carried out with changing of the dressings as required, (ii) dressings on donor sites until healing was complete or virtually complete. In addition, it is anticipated that these materials would be useful as dressings on debrided second degree burns until healing was complete or nearly complete. The sterilized dressings could be made available in sealed pouches which could be stored at ambient temperature and relative humidity, and they could be used as soon as they had been removed from the pouches. The packaged dressings could be used in any medical facility capable of treating individuals who have suffered major burns.

Any person skilled in the art will realize that the advantages of the materials of this invention will be enhanced by the incorporation of various bactericides or other suitable medicaments which can diffuse out of the films into the wounds. It is appreciated that a strengthening of the films by any of the polymer crosslinking procedures known to those skilled in the art, such as gamma irradiation, is within the scope of the invention. It will also be appreciated that although this description emphasizes the utility of the materials according to the invention as burn dressings, they can also be employed in the treatment of major skin discontinuities not due to thermal injury.

A common method of improving the flexibility of films of water-soluble polymers is to add a compatible plasticizer such as glycerol. It is believed that in many cases such additives cause plasticization of polymeric films by increasing the amount of water that they contain at equilibrium rather than by acting as plasticizers themselves. Part A of Table I below shows the effect on flexibility of the addition of various plasticizers to gelatin/PEI and gelatin/PEO films.

The pH of the standard solution which is cast to form gelatin/PEI films is about 10.5. Part B of Table I below shows the effect of adding various acids to change the pH of the standard solution used to prepare the gelatin/PEI film.

TABLE I

Flexibility properties of modified gelatin/PEI and gelatin/PEO films.

Part A. Effect of plasticizers on gelatin/PEI and gelatin/PEO films. (see note 1)

| | | | Flexibility at 20° C. and 46% relative humidity (see note 2) | | |
|---|---|---|---|---|---|
| Film label (batch #) | Film composition | Test film thickness (mm) | Fractures when cut with scissors | Number of successive creases causing fracture (see note 3) | Weight (g) required to force 15 mm wide sample through 6.5 mm gap (see note 3) |
| DGM-F-78-A (a) | gel./PEI 1:1 | 0.131 ± 0.001 | yes | 1 | 40.4 |
| DGM-F-87-A (a) (see note 8) | gel./PEI/ sorbitol 5:5:2 | 0.130 ± 0.002 | yes | 1 | 23.2 |
| DGM-F-78-B (a) | gel./PEI/ glycerol 5:5:2 | 0.130 ± 0.001 | no | >6 | 13.0 |
| DGM-F-81-A (b) | gel./PEI 1:1 | 0.130 ± 0.001 | yes | 1 | 33.8 |
| DGM-F-81-B (b) (see note 6) | gel./PEI/ PEG-1500 5:5:2 | 0.133 ± 0.002 | yes (slight) | 2 | 37.8 |
| DGM-F-82-A (b) (see note 7) | gel./PEI/ PEG-300 5:5:2 | 0.162 ± 0.001 (see note 4) | no | 3 | 31.2 |
| DGM-F-85-A | gel./PEO | 0.091 ± 0.001 | no | >6 | 37.8 |

TABLE I-continued

Flexibility properties of modified gelatin/PEI and gelatin/PEO films.

| | | | | | |
|---|---|---|---|---|---|
| (c) DGM-F-88-C (c) | 7:5 gel./PEO/ sorbitol 7:5:2.5 | 0.091 ± 0.001 | no | >6 | 24.6 |
| DGM-F-88-A (c) | 7:5:2.5 gel./PEO/ PEG-300 7:5:2.5 | 0.092 ± 0.001 | no | >6 | 18.0 |
| DGM-F-88-B (c) | 7:5:2.5 gel./PEO/ glycerol 7:5:2.5 | 0.091 ± 0.001 | no | >6 | 9.8 |

Part B. Effect of lowering pH of gelatin/PEI solutions (Note 1) with various acids before casting.

Flexibility at 20° C. and 46% relative humidity (see note 2)

| Film label (batch #) | Acid added; pH of solution before casting | Test film thickness (mm) | Fractures when cut with scissors | Number of successive creases causing fracture (see note 3) | Weight (g) required to force 15 mm wide sample through 6.5 mm gap (see note 3) |
|---|---|---|---|---|---|
| DGM-G-12-A (d) | none; 10.5 | 0.128 ± 0.002 | yes | 2 | 21.6 |
| DGM-G-13-A (d) | $H_2SO_4$; 7 | 0.130 ± 0.002 | no | 4 | 27.2 |
| DGM-G-12-B (d) (see note 5) | citric; 8.5 | 0.130 ± 0.001 | yes | 1 | 24.6 |
| DGM-F-86-A (e) | none; 10.5 | 0.129 ± 0.001 | yes | 1 | 33.8 |
| DGM-F-86-C (e) (see note 9) | $H_3PO_4$; 7 | 0.130 ± 0.001 | yes | 6 | 36.4 |
| DGM-F-86-B (e) | HCl; 7 | 0.130 ± 0.001 | no | >6 | 6.2 |
| DGM-G-3-A (f) | none; 10.5 | 0.130 ± 0.001 | yes | 1 | 28.2 |
| DGM-G-3-B (f) | HCl; 9.5 | 0.128 ± 0.001 | no | >6 | 14.0 |
| DGM-G-3-C (f) | HCl; 8.5 | 0.130 | no | >6 | 7.4 |
| DGM-G-3-D (f) (see note 4) | HCl; 3.5 | 0.147 ± 0.001 | no | 1 | 21.6 |

Footnotes to Table I
1. For gelatin/PEI films, gelatin was Bloom #150 (retail grade) from Davis Gelatine Co. For gelatin/PEO films, gelatin was Knox Brand, Bloom #250 from Thomas J. Lipton Ltd. PEI was Polymin P ® from BASF and PEO was Polyethylene Glycol Compound 20M (MW 15,000–20,000) from Union Carbide. For Part B, gelatin/PEI film used is in a weight ratio of 1:1.
2. Films were equilibrated at 20 ± 2° C. and 46 ± 2% relative humidity for 10 hours prior to the tests.
3. See text.
4. Note that the thickness of these films differs considerably from the others within their batch.
5. Citric acid was added until the solution became milky, at which point the pH was 8.5. The composition of the mixture was gelatin/PEI/citric acid = 2.1:2.1:1.
6. PEG-1500 is polyethylene glycol of molecular weight 1500. The film was very hazy.
7. PEG-300 is polyethylene glycol of molecular weight 300. The film was slightly hazy.
8. Sorbitol is $HOCH_2$—$(CHOH)_4$—$CH_2OH$, molecular weight 182.
9. The $H_3PO_4$ produced a cloudiness at about pH 8 which increased as the pH was lowered further to 7. The dry film from the cloudy solution was clear.

A method was devised which permits rapid flexibility measurements to be made. The numbers obtained are dependent on film thickness, and consequently measurements were carried out as far as possible on samples of the same thickness. A simple device (not shown) having two sets of wheels of diameter 9 mm were placed on parallel axles so that the gap between the wheels, when pushed away from each other against their respective axles, was 6.5 mm. The test film was placed on top of the two sets of wheels and a rod 5.0 mm in diameter was placed on the film perpendicular to its length and parallel to and between the two axles. Weights were placed at both ends of the rod. The combined weight of the rod and the weights which caused the film to bend enough to drop between the rotating wheels was taken as an indication of the flexibility. In practice, the rod was placed gently on the film and observed for a period of 10 seconds. If the film did not bend enough to allow the rod to pass through the gap, the rod was removed, weights were added at the ends in dumbell fashion, and it was gently placed on the film again. This was repeated until the rod fell through. In three cases, after the measurement had been completed on a sample, the same specimen was turned over and the measurement was repeated by bending the film in the opposite direction. The same results were obtained.

The value given by this method is a function of the width of the film as well as the thickness, and a standard width of 15 mm was used. The length of the test specimen was about 30 mm. A rotating wheel system was chosen because there would be a substantial friction force if the film had to pass between a gap defined by immovable surfaces. The results are tabulated in Table I above.

In addition to a flexibility test, it was desirable to have a simple procedure for measuring the relative brittleness of the film materials. Two tests were used. One was an examination of the edges of the film for fracture lines after cutting with high quality scissors. The other was a crease test in which one end of a specimen was folded to meet the opposite end and the loop between the joined ends was pinched tightly between thumb and forefinger. The same ends of the film were then moved to fold the film in the opposite direction, and the loop was pinched along the same crease line as before. This was repeated until the film had broken completely at the crease line. The test was stopped if the film had not broken by the sixth creasing. Most of the films which have a value of "6" in Table I showed no sign of fracture after the sixth creasing.

Results given by all three of the above tests depend on the moisture level in the film. All of the films in Table I were exposed to an atmosphere of 20±2° C. and 46±2% relative humidity for 10 hours immediately prior to, and during, the tests.

Results

For both the gelatin/PEI and gelatin/PEO films, glycerol was the most effective plasticizer. Polyethylene glycol-300 and particularly polyethylene glycol-1500 (numbers referring to molecular weights) were poorly compatible with the 1:1 mixture of gelatin and PEI.

The great improvement in flexibility caused by the adjustment of the gelatin/PEI solution of pH 7 was unexpected. The use of the polybasic acids $H_2SO_4$ and $H_3PO_4$ appeared to decrease flexibility as measured by the weight required to force film specimens through a 6.5 mm gap, but slightly increased the brittleness as assessed by the crease test. Citric acid was added until the solution become cloudy; the pH at that point was 8.5. Citric acid also caused, if anything, a decrease in flexibility.

Many of the modified films were subjected to short term adhesion tests on experimental wounds. In general, the modified films were as good as the standard films in terms of initial adhesion, but were not as good after a period of two hours because of a reduction in either adhesion or physical properties. The gelatin/PEI film obtained from a solution adjusted to pH 7 with HCl appeared to be the best of the modified films tested. This, combined with its superior flexibility, makes it a preferred material.

It has also been found that the preformed films according to the invention have bacteriostatic activity. For example, the bacteriostatic activity of a 0.16 mm thick sample of the preferred gelatin/PEI film described at page 7, line 28 to page 8, line 5 was demonstrated as follows. Agar plates were flooded with a broth culture of a test organism. Excess broth was sucked off and a disc 5 mm in diameter of the gelatin/PEI film was placed on top of the thin layer of organisms. The plates were then incubated at 37° overnight (about 18 hours) and examined for zones of inhibition of microbial growth. Two gram-positive bacteria, two gram-negative bacteria, and two fungi were tested. The film exhibited substantial inhibition of the growth of all six organisms. They were: *Micrococcus luteus, Staphylococcus aureus, Escherichia coli, Pseudomonas aeruginosa, Candida albicans,* and *Paecillomyces variotii. P. aeruginosa, S. aureus,* and *C. albicans* are three of the most common burn wound pathogens.

EXAMPLE 2

1 part of de-ionized gelatin of Bloom #300 from KIND and KNOX was dissolved in 9 parts of distilled water at about 50° C. and this solution was mixed with a solution of 2 parts of a commercial 50% aqueous solution of PEI (Polymin P ® made by BASF) in 10 parts of distilled water. The resulting solution was cooled to 25°–30° C. and poured onto a flat, smooth sheet of polystyrene and left to dry in air at room temperature. When dry, the thickness of the film was about 0.18 mm.

Aqueous Coatings

More specifically, an aqueous solution of 1 part gelatin of Bloom #150 and 2 parts of "Polymin P ®" (equivalent to 1 part PEI as Polymin P ® is supplied as a 50% aqueous solution) can be poured directly onto a debrided or undebrided burn wound where it sets to a gel which dries to form an adherent film. It is preferable to have a more concentrated gelatin-PEI solution than that described in Example 1 for the preparation of a preformed film because (i) more concentrated solutions have increased viscosity and are less likely to flow away from the surface of a wound after application, (ii) concentrated solutions produce thicker dry films for a given thickness of liquid applied and (iii) they dry faster. Because gelatin and PEI form a strong complex, there is an upper limit to the concentration of aqueous gelatin and aqueous PEI solutions which can be mixed at a given temperature. For example, an aqueous solution containing 36% w/w of polymers, specifically 72 g of Polymin P ® (50% aqueous solution) mixed with a warm solution of 36 g of gelatin of Bloom #150 in 90 ml of distilled water, resulted in a tough, rubbery, translucent material which separated immediately from solution. In general, the upper limit of the solids concentration will in most cases be the maximum possible concentration permitted by the solubility of the complex of gelatin and PEI in water at the temperature of application, i.e. about 30° C. Other things being equal, the higher the concentration the stronger the initially formed gel and the thicker the final dry film.

As the concentration of polymers is decreased, the dry film becomes thinner not only because the applied liquid film has less dissolved polymer, but also because the liquid film will be thinner because of reduced viscosity. For gelatin of Bloom #150 and Polymin P ®, it is contemplated that a total polymer concentration of 10% w/w would give too thin a film. For practical purposes, in the case of a single coating, 15% w/w is contemplated as the lower limit for this pair of polymers.

EXAMPLE 3

An aqueous gelatin-PEI (1:1) complex which has been used successfully in trials on experimental wounds contains approximately 22% w/w of the polymers, i.e. PEI plus gelatin. It is prepared and applied as follows: 30 g of Polymin P ® were diluted with 40 ml of distilled water and warmed to about 35° C. 15 g of gelatin of Bloom #150 (Davis Gelatine Co.) were dissolved in 50 ml of distilled water at about 50° C. This solution was added with stirring to the warm PEI solution. Stirring was continued for about 7 minutes while the mixture was kept in a bath of about 35° C. The clear, light yellow solution formed a gel after it had cooled to near room temperature. This gel can be conveniently melted by warming it in a bath of water from a hot water tap (frequently around 50° C.). A bath having a lower temperature, say 40° C., may also be used, but the rate of melting will be reduced. In any case the temperature of the liquid at the time of application should not be much higher than 30° C. In practice, a small amount of liquid is poured directly onto the wound and spread substantially uniformly over the surface of the wound and the healthy skin immediately surrounding the wound. A convenient technique is to simply spread the liquid with a hand covered with a sterile surgeon's glove, but a brush or other spreading device could also be used. If desired, a second coat of the liquefied gelatin-PEI gel can be applied on top of the first coat after it has dried.

Although the thickness of the dried film varies over the area of the wound because of the curvature and irregularity of the wound, the operable thickness range is about 0.05 to 0.30 mm, preferably about 0.18 mm.

EXAMPLE 4

The same procedure is followed as in example 3. However in this case the amount of polymers is 24% w/w, the Polymin P is diluted with 35 ml of distilled water and warmed to about 55° C., the gelatin is dissolved in 45 ml of distilled water at about 50° C., and stirring of the gelatin-PEI mixture is conducted in a bath at about 50° C.

EXAMPLE 5

The same procedure is followed as in example 3. However, in this case, the amount of polymers is 18.8% w/w, the Polymin P is diluted with 35 ml of distilled water and warmed to about 55° C., the gelatin is of Bloom #275 and grade H4S and is dissolved in 45 ml of distilled water at about 50° C. Moreover, when the gelatin/water solution was added with stirring to the warm PEI solution, a weak gel formed. To this were added 35 ml of distilled water and the mixture was stirred at about 50° C. for 10 minutes, yielding a liquid which would flow readily.

EXAMPLE 6

The same procedure is followed as in example 3. However, in this case the amount of polymers is 19% w/w, 20 g of Polymin P were diluted with 35 ml of distilled water and warmed to about 55° C., 10 g of de-ionized gelatin of Bloom #300 (KIND and KNOX) were dissolved in 40 ml of distilled water at about 50° C. and stirring was continued for about 10 minutes while the mixture was kept at about 50° C.

The embodiment of example 4 is preferred because the resulting increase in viscosity reduces the tendency of the applied liquid to flow away from the wound site. Although the viscosities of the formulations of examples 5 and 6 are adequate, they are somewhat inferior to that of example 4 in terms of convenience of application and produce thinner films.

It will be appreciated from the following examples that PEI's other than Polymin P which have the requisite properties including water solubility and molecular weight in the range of 10,000 to 100,000 would also be useful in burn wound dressings. Other PEI's include CORCAT P-600 which is a trademark for a PEI of molecular weight of 40,000 to 60,000, and CORCAT P-150 which is a trademark for a PEI of molecular weight in the range of 10,000 to 20,000, both of which are manufactured by the Cordova Chemical company of Michigan, may also be employed.

EXAMPLE 7

A useful liquid wound dressing employing CORCAT P-600 was prepared as follows: 10 g of gelatin of Bloom #150 (Davis Gelatine Co.) were dissolved in 45 ml of distilled water. 30 g of CORCAT P-600 as supplied by the manufacturer (a 33% aqueous solution) was diluted with 15 ml of distilled water and the solution was heated to 45° C. The gelatin solution, at 44° C., was added to the PEI solution and the mixture was stirred manually with a rod for 4 minutes. At the end of this time the gelatin-PEI complex had made the solution too viscous, and it was diluted with 15 ml of distilled water to improve its flow properties. It formed a gel as it cooled to room temperature.

EXAMPLE 8

Another liquid wound dressing was prepared with CORCAT P-150. 10 g of gelatin of Bloom #150 (Davis Gelatine Co.) were dissolved in 45 ml of distilled water. 30 g of CORCAT P-150 as supplied by the manufacturer (a 33% aqueous solution) were warmed to 42° C. and added to the gelatin solution heated to 39° C. The mixture was stirred manually with a rod for 4 minutes. At the end of this time it was relatively non-viscous, and formed a gel as it cooled to room temperature.

In order to demonstrate the effectiveness of these two materials as wound dressings, they were tested on model wounds on a juvenile domestic pig weighing about 24 kg. Six 3×3 cm areas of healthy skin on the top of the back were excised down to about the middle of the top layer of subcutaneous fat. Hemostasis was achieved by cauterization as needed. Wounds 3, 4, and 6 received the dressing with CORCAT P-600, wounds 1 and 5 received the dressing containing CORCAT P-150, and wound 2 received a control dressing containing Polymin P which was prepared according to Example #3. Gel samples of all three materials in sealed polyethylene bags were melted by placement in a water bath at about 35°–40° C. and spread over the wounds and healthy skin immediately surrounding them. The performance of the wound coverings was followed for 6 days after application. During this time, all three materials remained very adherent to the wound surface and functioned very effectively as wound coverings. The dressing prepared with CORCAT P-150 was relatively non-viscous when the gel was melted prior to application, and for that reason it flowed under the influence of gravity much more than the others and produced a much thinner wound covering. The use of a more concentrated solution or application of two coats would have been preferred.

The time required for the liquefied gel of the present formulation to set a gel after application to the debrided burn wound depends on several factors. In our experience, provided that (i) the film of applied liquid is not too thick and is uniformly spread, (ii) bleeding of the wound has been arrested, and (iii) the temperature of the liquid is about 30° C. at the time of application, the liquid sets to a gel in about 20 minutes. This gel, which is not tacky, then dries to a clear, supple film which has excellent adhesion to the wound. Gelation and drying of the liquid film covering healthy skin near the edges of the wound is much faster because much less water passes through healthy skin than through a freshly debrided wound.

A frequently used experimental wound on domestic pigs has been a full thickness, third degree burn freshly excised to subcutaneous fat 5 to 7 days post burn. When the gelatin-PEI liquid coatings described in examples 3–6 are spread on a wound of this type they dry to films which remain intact and adherent for generally 7 days or more One dressing formed by the application of two coats of the liquid embodied in example 3 lasted for several weeks. In no case has purulence been observed beneath the dressings during the period in which they remained intact and adherent.

Comparison of Aqueous Gelatin-PEI Complexes with Dressings of (i) Gelatin Alone, (ii) PEI Alone, and (iii) Preformed Gelatin-PEI Complex Films A solution of gelatin alone will dry after having been coated on a wound surface, but the resulting film is inferior to that produced when a solution of PEI combined with the same grade of gelatin dries on the wound. This is illustrated by the following in vivo experiment carried out on a juvenile domestic pig weighing about 60 pounds.

Six areas of healthy skin, each measuring 37×37 mm, were removed from the back by excision down to subcutaneous fat. Three wounds on the left side of the spine were given odd numbers (1, 3, and 5), and the three wounds on the right side were given even numbers (2, 4, and 6). Wounds 1 and 2 were related by bilateral symmetry about the spine, as were 3 and 4, and 5 and 6. The wounds were divided into two groups of 3 each: 1, 4, and 5; and 2, 3, and 6. One group (1, 4, and 5) was selected by chance to receive the 22% w/w gelatin-PEI (1:1) solution described in Example 3 above. The other group (2, 3, and 6) received a 31% w/w solution of the same grade of gelatin used in the gelatin-PEI solution placed on sites 1, 4, and 5. (It should be noted that the significantly higher concentration of the gelatin solution is made possible because of the difference in viscosity and gelation properties between it and the gelatin-PEI complex.) No additional dressing materials of any type were placed on the wounds; they were protected from mechanical injury by a device which was secured to the back of the animal and allowed free access of air to the wound area.

After three days, wounds 2, 3, and 6 (gelatin) had peripheral areas in which there were pools of turbid liquid. Of the set of wounds covered with gelatin-PEI, only #5 had liquid of this type, and that was a small amount at one edge. The films on sites 1, 4, and 5 (gelatin-PEI) were more supple than the gelatin only films. After 10 days, all of the films were removed and the normal preparation for skin grafting was carried out (removal of loose material and non-viable tissue, application of moist saline gauze to draw fluid from the wound, etc.). The most striking feature of the gelatin only sites (2, 3, and 6) as a group was their reduced size due to contraction. Prevention of contraction is an extremely important aspect of burn wound care, because contraction causes not only disfigurement but also reduced mobility. Contraction of wound #6 was the most marked. On that site the film had completely lost its adhesion, and beneath a covering of crusty exudate there was a turbid, viscous fluid. The white areas observed in sites 2 and 3 were ones in which the gelatin film retained its adhesion.

A coating of a solution of PEI alone will not dry out to form a useful film. Even when exposed to an atmosphere of about 40% relative humidity on a flat sheet of plastic at room temperature for 10 days the film did not dry out sufficiently to be useful as a burn wound dressing. Specifically, the film was soft and sticky, and if it had been formed in situ on a patient's wound it would not be acceptable for clinical use because it would adhere to bedding, etc.

The gelatin-PEI aqueous coating form is thus preferred and forms a wound dressing which is superior to the preformed gelatin-PEI films. The superiority is almost certainly due to the ability of the liquid coating to completely cover the wound surface because it can flow into the crevices and depressions. This means that for a given wound area, the total area in contact with the dressing formed from the liquid will be greater than the area in contact with the preformed film. The increased area of contact will, other factors being equal, produce improved adhesion. In addition, the air pockets between the film and the wound which occur in the case of the preformed film can become filled with liquid and may become pockets of infection. Also of note is that the liquid coating adheres to healthy skin and to undebrided burn wounds, making possible its use as a first aid dressing.

The only apparent disadvantage of the gelatin-PEI liquid coating when compared to the preformed film is that it requires some time to gel and then dry on the wound. One method applicant has found for circumventing this is to apply a preformed gelatin-PEI film of the preferred formulation, on top of the freshly applied gelatin-PEI liquid coating before it sets to a gel. The liquid can then gel, and dry by transmission of water vapour through the preformed film above it. Preformed gelatin-PEI films of thickness 0.10 and 0.17 mm have been used successfully in combination with the gelatin-PEI liquid. It is expected that films thinner than 0.10 mm will become excessively soft and tacky when placed on the freshly applied coating of liquid and consequently will offer no advantage over the use of the liquid alone.

When the coating of liquid beneath the preformed film has dried, it has good adhesion to the preformed film, and the combination of the two adherent films serves as the wound dressing until removal of the dressing is desirable. On occasion it has been possible to pull the outer layer of preformed film away from the inner layer of dried gel which remained adherent to the wound.

It is felt that, in addition to a preformed gelatin-PEI film, other resin film materials which are highly permeable to water vapour might serve as a useful outer covering for the freshly applied coating of gelatin-PEI liquid. Other preformed films which could be employed include Celgard ® a microporous polypropylene material made by Celanese, and fine nylon mesh material as employed in commercial stockings. These film materials could remain in place when the liquid had dried if their physical properties were suitable, or depending upon their adhesion, they could be peeled away.

It is contemplated that the limits of weight ratios in the gelatin-PEI liquid which will still give an outstanding wound dressing is (gelatin-PEI) 7:3 to 3:7; compared to ratios for the preformed gelatin-PEI film of 9:1 to 3:7.

Separation of Gelatin and PEI Components Until Application to Wound

One of the problems associated with gelatin PEI dressings applied in the aqueous coating format is their relatively short shelf life at room temperature. Such materials are particularly vulnerable to autodegradation, which is almost certainly caused by hydrolysis of gelatin in the highly alkaline environment. Although this drawback is not necessarily a major one in the clinical setting where refrigeration and regular monitoring of expiry dates may be expected, it is hardly accpetable for use in the field where maintenance of properties under extreme conditions of climate is desirable if not essential.

This problem may be overcome by maintaining the gelatin and PEI components apart and then bringing them together to form the aqueous coatings at the time of use. In-line static mixing devices are currently on the market. Devices of this type are ideally suited for dispensing delayed set liquid materials. One such device includes twin syringes, one of which is filled with the solution to be set, and the other is filled with the setting agent. Simultaneous extrusion of the two liquids through a disposable static mixing tube associated with the device is an effective and very convenient method of mixing the component liquids.

Since gelatin/PEI complexes are homogeneous mixtures of an aqueous solution of gelatin and an aqueous solution of PEI, these two components could be packaged separately in the two chambers of the twin syringe and mixed by co-extrusion at the time of application to the patient.

The separation of the gelatin from the PEI not only offers the advantage of a dramatic improvement in shelf life, but also provides other opportunities for improving the burn wound dressing material. Specifically, the polymer concentrations in the present formulations of gelatin/PEI complexes are the highest which can be obtained by mixing aqueous solutions of the ingredients at a room temperature of about 50° C. Attempts to achieve higher concentrations result in the formation of a tough, rubbery gel when the two solutions are mixed. This has been unfortunate, because a more concentrated solution of the gelatin/PEI complex would give a coating which would set faster and dry more quickly on the wound. It has been observed, however, that there is a delay in the formation of this intractable gel when the gelatin and PEI are mixed. Although quite small, this delay appeared to be sufficient to allow delivery of a more concentrated gelatin/PEI dressing to the wound site by in-line mixing of more concentrated gelatin and PEI solutions. It is not likely that high viscosity solutions will interfere with the efficient operation of the in-line mixing device, since it is typically used to dispense a very viscous dental impression material. On the other hand, it should be noted that inadequate mixing may be expected when two solutions of significantly different viscosity are used.

Experiments along these lines, summarized in Table 2, have been very encouraging. The first in-line mixed gelatin/PEI complex, named MED-201LT, was prepared using a 25% increase in the total polymer concentration (as parts per hundred parts of water) compared with the formulation of MED-201L as identified specifically hereinafter. Within 6 minutes after extrusion onto an area of healthy skin, MED-201LT formed a strong, tough, elastic covering which could withstand significant abrasion, although there did seem to be a reduction in the adhesion properties of the film when dried.

The gelatin solution in one of the chambers of the twin syringe will be in the form of a gel at room temperature which must be melted before application of the dressing. The melting process can normally be accomplished fairly easily be employing various conventional heat sources to elevate the temperature of the gel to 45°–50° C. Before co-extruding the two liquids through the in-line mixing tube onto the wound, their temperature should be allowed to fall, preferably by 10° or 20° C., but not so low that the gelatin solution reverts to a gel.

Aqueous Gelatin-PEI Complexes with Reduced pH

Although gelatin-PEI liquids with a 'natural' pH are effective burn wound dressing materials, formulations with reduced pH are also effective. As in the case of the preformed films, a suitable acid for pH reduction is concentrated hydrochloric acid. One formulation, whose pH was reduced to 8 with hydrochloric acid, has been found to be very effective in in vivo experiments; it has been designated MED-203L (see Nomenclature).

An effective two-component liquid designated MED-203LT (see Nomenclature) consists of a gelatin solution and a separtate PEI solution adjusted to pH 9. Co-extrusion of the two components through the mixing tube gives a burn wound dressing with a pH somewhat lower than 9 because of the particular gelatin employed (see Table 2, footnote a.).

It is contemplated that suitable gelatin-PEI burn wound coatings will have a pH in the range 8–11 when applied to the burn wound.

TABLE 2

Properties of gelatin/PEI formulations dispensed from an in-line mixing device (see text) onto a small area of healthy skin.

| Entry # | Solutions$^e$ placed in the in-line mixing device | | Dressing Name | Observations$^f$ |
|---|---|---|---|---|
| | Chamber 1 | Chamber 2 | | |
| 1 | 40%$^e$ PEI$^b$ (pH 11.5)$^c$ | 40%$^e$ gelatin$^a$ | MED-201 LT | Spreadability only fair due to coherence. 6 min: strong, tough, elastic, moderately tacky gel. 30 min: not tacky, not dry. 2 hr: film dry, clear, flexible. 6.3 hr: 10% of area had lost its adhesion. |
| 2 | 33% PEI$^b$ (pH 9.0)$^d$ | 40% gelatin$^a$ | MED-203 LT | Spreadability was good. 6 min: moderately strong and very tacky. 25 min: slightly tacky. 35 min: dry, clear, not tacky, somewhat stiff and brittle. 8.5 hr: 1% of area had lost its adhesion. |

Footnotes
$^a$Gelatin was the retail grade of the Davis Gelatine Co., Bloom #150, pig skin, Type A.
$^b$PEI was Polymin P ™ (BASF) with a molecular weight of about 50,000. It was obtained from BDH Chemicals as product #15047.
$^c$Natural pH.
$^d$The pH was lowered by adding concentrated HCl.
$^e$Concentrations are expressed as parts per hundred parts of water.
$^f$The coatings applied to healthy skin were allowed to dry in the normal laboratory atmosphere. The relative humidity in most cases was around 20%.

Nomenclature

MED-201L: Gel (at room temperature) composed of
    15 parts gelatin of Bloom #150,
    15 parts PEI of MW 50,000,
    95 parts water, at "natural" pH of 10.5.

MED-201LT: Two liquids (when warm) stored in separate chambers of a twin syringe.
Chamber One:
  4 parts PEI of MW 50,000,
  10 parts water,
  at "natural" pH of 11.5.
Chamber Two:
  4 parts gelatin of Bloom #150,
  10 parts water.

MED-203L: Gel (at room temperature) composed of
  3 parts gelatin of Bloom #150,
  3 parts PEI of MW 50,000,
  32 parts water,
  at pH adjusted to 8 with HCl.

MED-203LT: Two liquids (when warm) stored in separate chambers of a twin syringe.
Chamber One:
  3.3 parts PEI of MW 50,000,
  10 parts water,
  with pH adjusted to 9 with HCl.
Chamber Two:
  4 parts gelatin of Bloom #150,
  10 parts water.

The embodiments of the invention in which an exclusive property or privilege is claimed is defined as follows:

1. A burn wound-adherent dressing material comprising a complex of gelatin of Bloom # of 80 to 350 and a water-soluble polyethylenimine of molecular weight of 10,000 to 100,000, in a weight ratio of gelatin to polyethylenimine of 7:3 to 3:7, said burn wound dressing material being in the form of a substantially uniform, aqueous coating which when applied to a burn wound sets to a gel and dries to a continuous wound-adherent film in situ.

2. A burn wound dressing according to claim 1, wherein the aqueous coating contains about 24% w/w of the total of polyethylenimine and gelatin.

3. A burn wound dressing according to claim 2, wherein the weight ratio of gelatin to polyethylenimine is about 1:1.

4. A burn wound dressing according to claim 3, wherein the thickness of the resulting film is about 0.18 mm.

5. A burn wound dressing according to claim 1, wherein the thickness of the resulting film is in the range of 0.05 to 0.30 mm.

6. A burn wound dressing according to claim 1, wherein the gelatin has a Bloom # of about 150 and the polyethylenimine has a molecular weight of 40,000 to 60,000.

7. A burn wound dressing according to claim 1, additionally comprising a preformed film of a complex of gelatin and polyethylenimine of a thickness of about 0.10 to 0.17 mm covering the freshly applied coating, wherein the weight ratio of gelatin to polyethylenimine is about 1:1.

8. A method of treating a burn wound on a person having a burn, which comprises applying to the burn wound a burn wound-adherent dressing material in an amount effective to form a continuous wound-adherent film, said dressing material comprising a complex of gelatin of a Bloom # of 80 to 350 and a water-soluble polyethylenimine of molecular weight of 10,000 to 100,000, in a weight ratio of gelatin to polyethylenimine of 7:3 to 3:7.

9. A method according to claim 8, wherein the dressing material is (a) applied to a burn wound at a temperature of about 30° C. in the form of an aqueous coating, (b) spread substantially uniformly over the surface of the wound, and (c) allowed to set to a gel and dry to a continuous wound-adherent film in situ.

10. A method according to claim 9, wherein the aqueous coating contains about 24% w/w of the total of polyethylenimine and gelatin.

11. A method according to claim 10, wherein the weight ratio of gelatin to polyethylenimine is about 1:1.

12. A method according to claim 11, wherein the gelatin has a Bloom # of about 150 and the polyethylenimine has a molecular weight of 40,000 to 60,000.

13. A method according to claim 12, wherein the thickness of the resulting film is in the range of 0.05 to 0.30 mm.

14. A method according to claim 13, wherein the thickness of the resulting film is about 0.18 mm.

15. A method according to claim 9, comprising the additional step of applying a preformed film of a complex of gelatin and polyethylenimine of a thickness of about 0.10 to 0.17 mm over the freshly applied coating, wherein the weight ratio of gelatin to polyethlenimine in said film is about 1:1.

16. A method according to claim 8, wherein the dressing material is applied to a debrided burn wound, in intimate contact with the wound, in the form of a continuous wound-adherent preformed film.

17. A method according to claim 16, wherein the weight ratio of gelatin to polyethylenimine is about 1:1.

18. A method according to claim 17, wherein the thickness of the resulting film is 0.05 to 0.35 mm.

19. A method according to claim 18, wherein the gelatin has a Bloom # of about 150 and the polyethylenimine has a molecular weight of 40,000 to 60,000.

* * * * *